United States Patent

Olsson et al.

[11] Patent Number: 5,497,767
[45] Date of Patent: Mar. 12, 1996

[54] METHOD AND APPARATUS FOR SUPPLYING FRESH GAS TO A PATIENT DURING MANUAL VENTILATION

[75] Inventors: Sven-Gunnar Olsson, Arloev; Goeran Cewers, Lund; Goeran Rydgren, Bunkeflostrand, all of Sweden

[73] Assignee: Siemens Elema AB, Solna, Sweden

[21] Appl. No.: 188,763

[22] Filed: Jan. 31, 1994

[30] Foreign Application Priority Data

Feb. 5, 1993 [SE] Sweden .................................. 9300364

[51] Int. Cl.$^6$ .................................................. A61M 16/00
[52] U.S. Cl. .................. 128/205.13; 128/205.14
[58] Field of Search .................. 128/203.12, 205.14, 128/205.13, 205.17

[56] References Cited

U.S. PATENT DOCUMENTS

| | | | |
|---|---|---|---|
| 3,307,542 | 3/1967 | Andreasen | 128/204.28 |
| 3,530,856 | 9/1970 | Bird | 128/205.14 |
| 3,537,450 | 11/1970 | Fox | 128/205.14 |
| 3,739,776 | 6/1973 | Bird et al. | 128/204.25 |
| 3,974,027 | 2/1974 | Johnson | 128/205.28 |
| 4,351,329 | 9/1982 | Ellestad et al. | 128/205.14 |

FOREIGN PATENT DOCUMENTS

| | | |
|---|---|---|
| 2813270 | 10/1979 | Germany. |
| 2062475 | 11/1980 | United Kingdom. |

*Primary Examiner*—Aaron J. Lewis
*Attorney, Agent, or Firm*—Hill, Steadman & Simpson

[57] ABSTRACT

In a method for supplying fresh gas in manual ventilation of a patient and in a ventilator system for practicing the method, the supply of fresh gas to a breathing bag is regulated. During inspiration, the breathing bag is squeezed, imposing an inspiration on the patient. A detector at the breathing bag senses when the patient exhales, and an identical flow of gas is fed to the system via an inspiratory valve, the flow of fresh gas is directed into the breathing bag and expired gas is prevented from entering the breathing bag. An expiratory valve simultaneously opens to conduct expired gas out of the system.

37 Claims, 3 Drawing Sheets

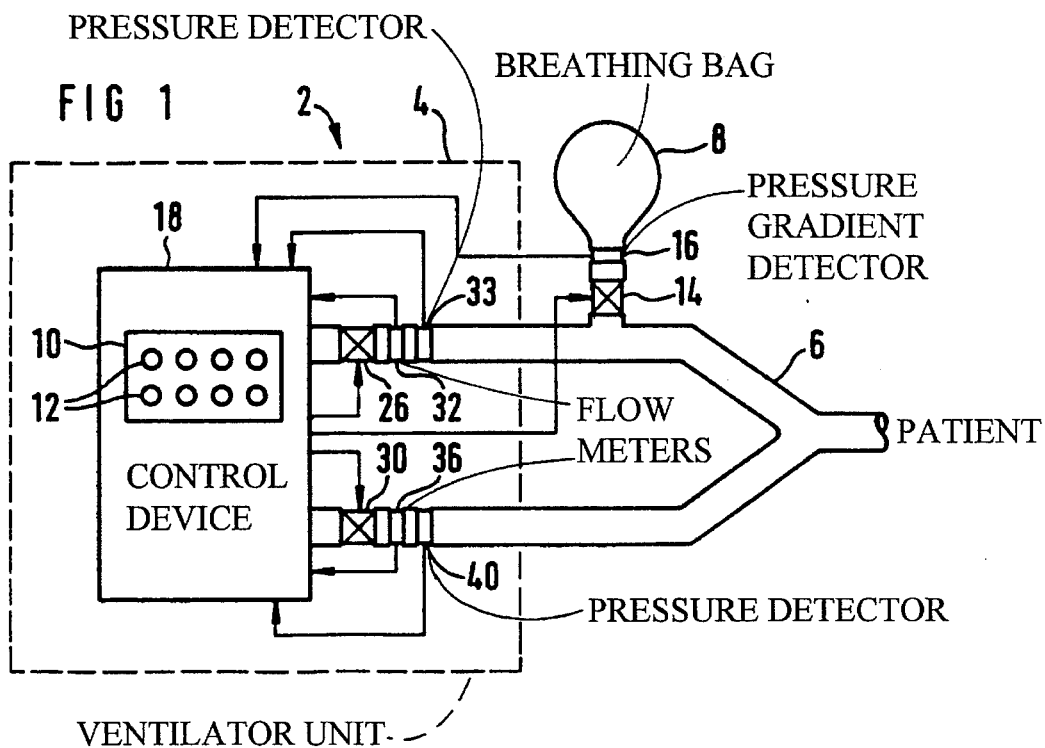
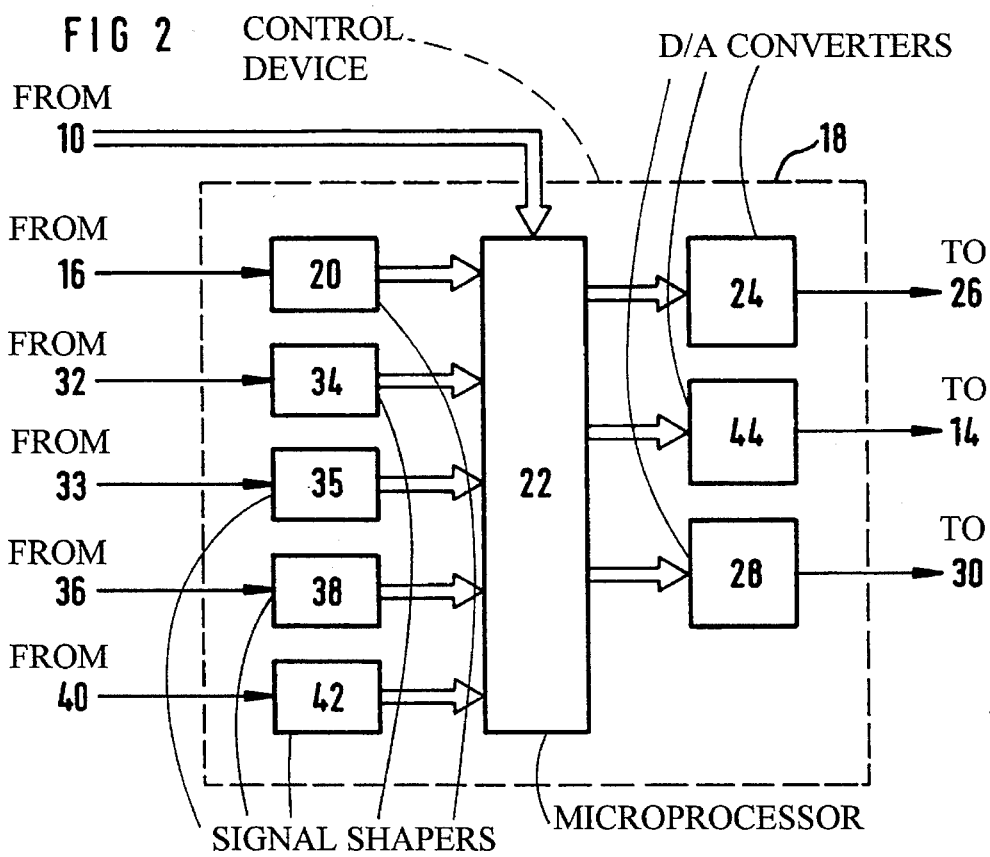

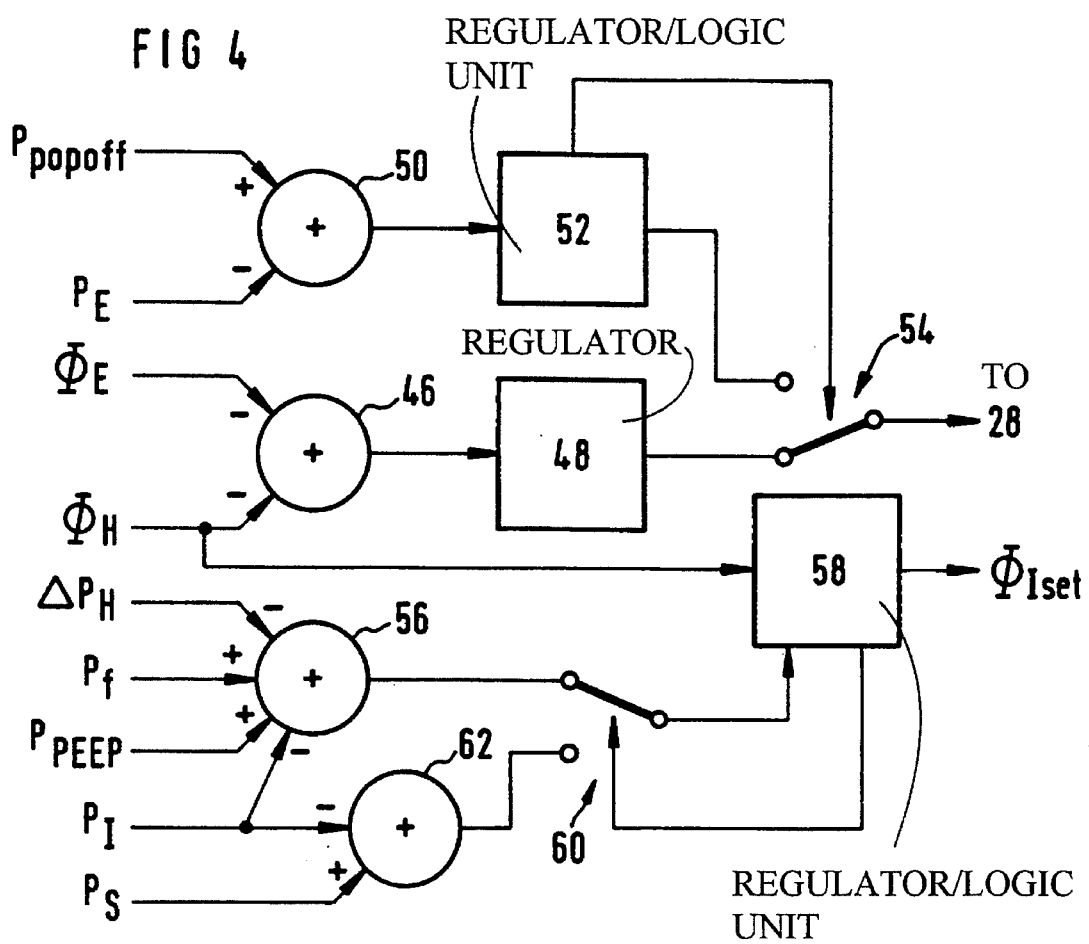
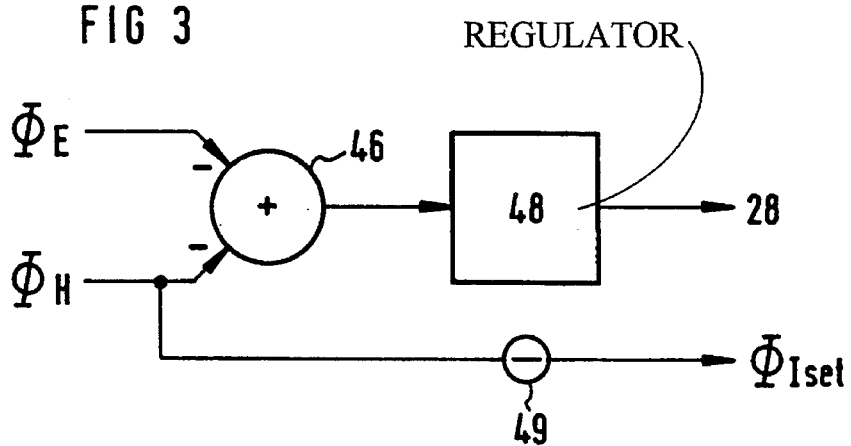

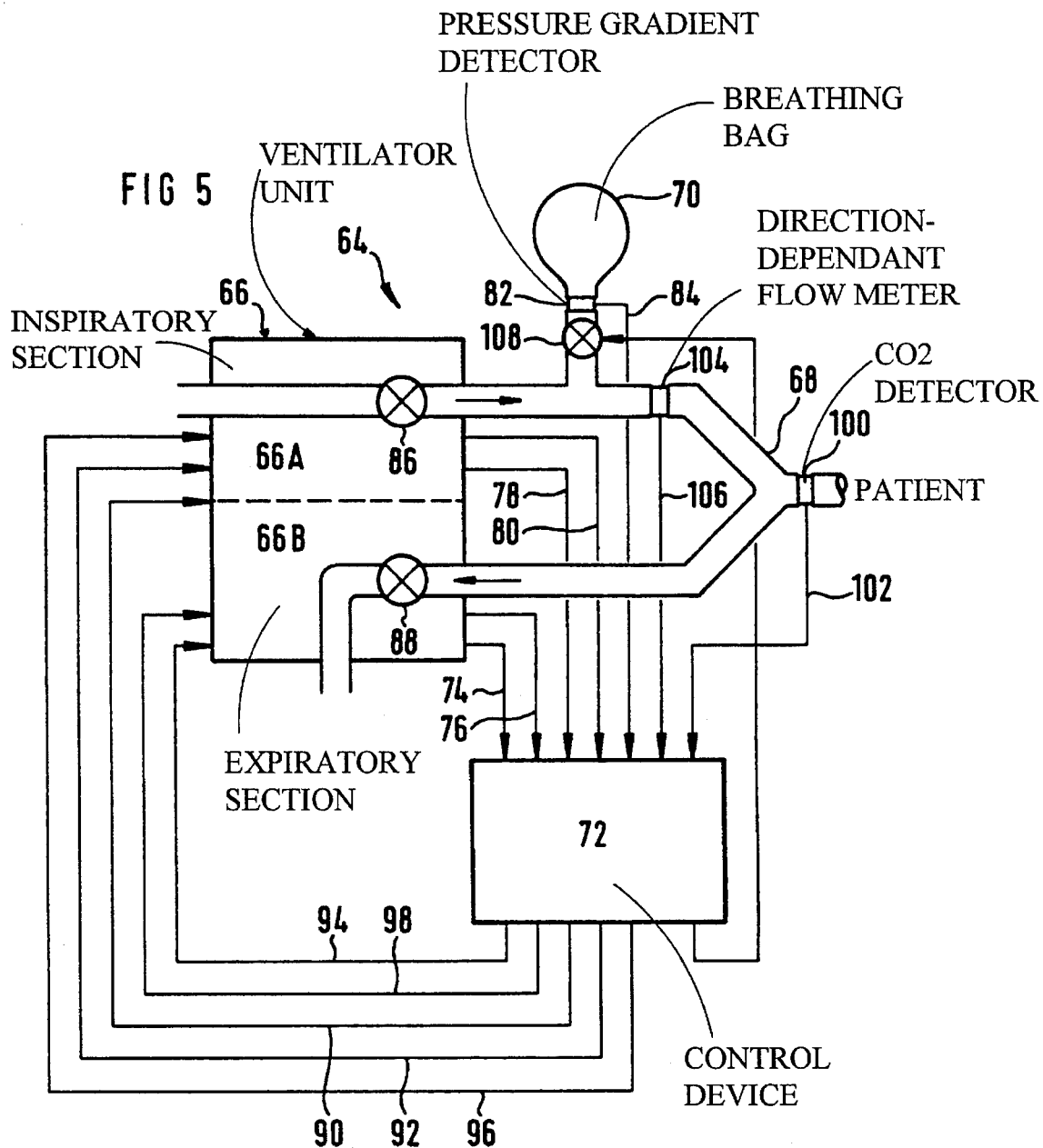

5,497,767

METHOD AND APPARATUS FOR SUPPLYING FRESH GAS TO A PATIENT DURING MANUAL VENTILATION

BACKGROUND OF THE INVENTION

1. Field of the Invention

The present invention relates to a method for supplying fresh gas, preferably for use with a ventilator system for manual ventilation of a patient, in which a breathing bag is squeezed to impose an inspiration on the patient.

The invention also relates to a ventilator system operable in accordance with the method.

2. Description of the Prior Art

Ventilator systems are used for facilitating, supporting or imposing inspiration and expiration on a patient. Manual ventilation is sometimes employed when inspiration and expiration are imposed on the patient, i.e., the physician controls the patient's inspiration and expiration by means of a breathing bag. When the breathing bag is connected to the patient's airways without any intermediate pressure exchange system, the physician is able to feel the response of the lungs to the action of the breathing bag. In other words, the physician can be said to communicate directly with the lungs. This is essential, particularly in anesthesia where the anesthetist wishes to control the entire respiratory process himself/herself.

In U.S. Pat. No. 3,794,027 a manual ventilation system for anesthesia. The system includes a breathing bag which the physician squeezes to push air through a patient tube to a patient, thereby imposing inspiration on the patient. When the physician relaxes her/his pressure on the breathing bag, air from the patient can return through a carbon dioxide absorber to the breathing bag. The entire time, the physician can feel the way the patient is breathing. The bag must be periodically detached from the system, emptied and refilled with fresh gas to replace the gas re-breathed a plurality of times by the patient. In the patient tube there are also two check valves, near the patient, which respectively control the direction of gas flow to and from the patient.

Periodic evacuation of the bag has numerous disadvantages. It means that control over the patient's respiration terminates during the time it takes to replace gas, and replacement distracts the anesthetist's concentration from the patient. Moreover, gas containing anesthetic leaks into the operating theater and can have an adverse effect on surgical staff.

SUMMARY OF THE INVENTION

An object of the present invention is to provide a method for manually ventilating a patient using a breathing bag which avoids the above-described disadvantages and in which the patient does not re-breathe her/his own expired gas, with no loss of the physician's ability to communicate with the lungs.

Another object of the invention is to provide a ventilator system for carrying out the method and which facilitates control of gas flow in the patient tube, making check valves and gas absorbers unnecessary.

One such method is achieved in accordance with the invention wherein fresh gas is fed into the breathing bag during expiration with a gas flow corresponding to the patient's flow of expired gas, and gas expired by the patient is conducted out of the ventilator system.

By replacing the gas inspired by the patient from the breathing bag with fresh gas as the patient exhales, there is no need for the anesthetist to disconnect the breathing bag periodically. Since fresh gas is fed into the breathing bag with the same flow profile as the patient's expiration, the physician will not notice any difference compared to the situation when the patient expires directly into the breathing bag. This filling method works equally well when the patient breathes spontaneously.

In a further embodiment of the method in accordance with the invention, a parameter related to the patient's expiration is measured between the patient and the breathing bag and gas flow is controlled according to the measured parameter.

Measurement of an expiration-related parameter between the patient and the breathing bag supplies direct information about when the patient commences expiration and about the course of expiration (the flow profile). A counterflow, identical to the patient's flow of expired gas, can then be supplied at the same time as the patient's expired gas is removed. Fresh gas is fed into the breathing bag with the same flow profile as the flow profile of gas expired by the patient. Expired gas is prevented from entering the breathing bag and forced out of the ventilator system. The slightest change in expiratory flow from the patient affects the parameter measured, and control of the flow of fresh gas can be directly adapted to such changes. In this way, the physician will not notice any difference compared to conventional ventilation wherein the patient expires gas directly into the breathing bag. For example, the physician can, by acting on the breathing bag, control the patient's expiratory profile so the flow of fresh gas adapts directly to expiratory flow regulated by the physician, i.e., it will feel to the physician as if the patient's lungs were communicating directly with the breathing bag, even though expired gas is conducted out of the ventilator system. Since expired gas is not re-breathed, no carbon dioxide filter is needed, and control of the direction of gas flow is achieved by control of the flow of fresh gas, making check valves unnecessary for controlling the direction of the gas flow.

In this context, it is preferable if the measured parameter is one of the parameters gas flow, temperature, relative gas humidity or concentration of a specific gas and is used as the control parameter.

These four variables are all specific for a patient's expiratory gas, e.g. gas flow, whose direction is toward the breathing bag in expiration, and temperature which, like relative gas humidity, is higher in expiratory air. The gases supplied to the patient are absorbed by the body, so measuring the oxygen concentration, carbon dioxide concentration or the concentration of some anesthetic, for example, supplies direct confirmation of the patient's expiration. The flow of fresh gas is then regulated according to the measurement of one of these parameters, e.g. by balancing flow so it increases as long as the parameter is detected and decreases when the parameter is not detected until the breathing bag has refilled and is again ready for the inspiration phase.

In a further embodiment of the method in accordance with the invention, an additional parameter is measured for starting control of the flow of fresh gas and/or starting a functional check on the method, and an alarm is generated and/or an alternative ventilation mode started if at least one defined condition is met.

In this manner, measurement of flow, for example, could be used for controlling the supply of fresh gas, this control starting when a carbon dioxide detector, for example, senses the presence of $CO_2$. The reason for this is to utilize a parameter providing a fast indication of when the patient begins expiration while simultaneously utilizing the most appropriate control parameter for regulating the supply of fresh gas. The safety feature obtained through functional control of the method means that if a fault occurs in, e.g. measurement of the control parameter so fresh gas is supplied at an erroneous rate or terminates completely, an alarm is generated drawing the staff's attention to the fault. Alternately, the system could be automatically switched to some other method, involving the monitoring of some other control parameter, or some other ventilation mode, e.g. mechanical ventilation.

A ventilator system for conducting the method is achieved in accordance with the invention having a patient tube connectable to the patient, a ventilator unit for controlling a flow of gas in the patient tube and a breathing bag connected to the patient tube, and a first parameter detector for sensing one of the parameters gas flow to/from the breathing bag or gas pressure in the breathing bag. The ventilator unit during expiration controls the flow of gas in the patient tube according to the gas flow or gas pressure measured by the first parameter detector so a flow of fresh gas, corresponding to the flow of gas expired by the patient, is fed into the breathing bag, and gas expired by the patient is conducted out of the ventilator system.

Since gas flow and gas pressure are directly interrelated, it does not matter which of the two parameters is measured and used to control the system.

An alternative embodiment of ventilator system in accordance with the invention includes a second parameter detector placed between the patient and the breathing bag for measuring a parameter related to patient expiration, preferably one of the parameters of gas flow, temperature, relative gas humidity or the concentration of a specific gas, and the ventilator unit during expiration controls the flow of gas in the patient tube according to the parameter measured by the second parameter detector, so a flow of fresh gas, corresponding to the flow of gas expired by the patient, is thus fed into the breathing bag, and the gas expired by the patient is conducted out of the ventilator system.

The difference between the two described embodiment of the ventilation system of the invention is that in the first system the flow to/from the breathing bag or the pressure in the breathing bag is measured, whereas in the second system a control parameter is measured in the patient tube between the breathing bag and the patient.

In both of these embodiments of the ventilator system according to the invention, the ventilator unit preferably includes a controllable inspiratory valve connected to one end of the patient tube, a controllable expiratory valve connected to the other end of the patient tube and a control device connected to the parameter detector and to the valves for the purpose of controlling the valves according to the parameter.

In principle, it is sufficient for practicing the method if the inspiratory valve passes a continuous flow and the ventilator system is controlled by regulation of the expiratory valve. The ventilator unit can be devised so the control device constitutes an integral part of the ventilator unit or so that a separate control device can be connected to a known ventilator, such as the Servo Ventilator 300 made by Siemens-Elema AB, Solna, Sweden.

Preferably the ventilator unit further includes a second detector for sensing gas flow or gas pressure at the inspiratory valve and a third detector for sensing gas flow or gas pressure at the expiratory valve, and the control device controls the valves according to the gas flows and/or gas pressures measured by the detectors. Measurement of flows, or pressures at the valves, makes it possible to control these valves more exactly.

In a further version of the ventilator system according to the first-described embodiment, the detectors sense gas flow, and the control device includes an integrator unit which integrates the gas flows sensed by the detectors in order to determine the gas volumes passing the respective detector during expiration, and the control device controls the valves so the determined gas volumes are essentially identical.

This ensures that the expired volume of gas is replaced by an equally large volume or fresh gas fed into the breathing bag. At the same time, information is obtained about the patient's inspiratory and expiratory volumes, and this information can be used by the anesthetist for deciding whether respiratory volume or respiratory rate should be increased, reduced or retained. Exact measurement of the gas flows also makes possible rapid detection of minor leaks in the system.

In this context, preferably the control device continuously zeroes the first detector, since this increases the detector's ability to detect small flows or low pressures. Zeroing corresponds to an AC coupling of the detector with a long time constant, lasting up to several minutes.

In the ventilator system according to both of the above-described embodiments, the control device can control the valves so a flow of fresh gas is passed through the patient tube during expiration.

Passing a flow of fresh gas through the patient tube flushes out any expired gas left in the patient tube between the breathing bag and lungs, i.e. dead space is reduced throughout the entire system.

In this version of the above-described embodiments, the control device preferably controls the valves so the flow of gas at the inspiratory valve is less than the flow of gas at the expiratory valve and a first pressure detector measures pressure in the breathing bag, and the control device regulates the inspiratory valve, so that when pressure in the breathing bag drops below a first defined pressure, a flow of gas for filling the breathing bag is fed into the patient tube.

This approach gradually regulates the system toward increasingly lower pressure until a filling pressure is achieved. This regulatory procedure prevents the build-up of pressure in the system. Pressure in the breathing bag can be measured directly by a manometer in the breathing bag, but since pressure in the breathing bag is directly related to pressure in the patient tube, pressure in the breathing bag can be determined by measuring the pressure gradient when flow is measured in the breathing bag and pressure is measured in the patient tube.

Alternately, it may be advantageous in certain instances for the control device to control the valves so that the flow of gas at the inspiratory valve is greater than the flow of gas at the expiratory valve and to employ a second pressure detector which measures pressure in the patient tube. The control device regulates the expiratory valve, when pressure in the patient tube exceeds a second defined pressure, to cause the pressure to drop.

This approach gradually regulates the system toward a definable maximum pressure, i.e. a pop-off pressure, and prevents the patient from being exposed to pressures greater than this maximum pressure.

In the ventilator system according to both of the above-described embodiments, in the control device can control the valves so as to pass a flow of fresh gas through the patient tube during inspiration.

In the same way as during expiration, a flow of fresh gas may be fed through the system during inspiration. A flow of fresh gas can naturally be present even throughout the entire inspiratory and expiratory cycle, i.e. during both inspiration and expiration, in order to flush out any residual gas expired by the patient.

In order to improve control of the system, preferably the breathing bag has a flow valve which is controllable by the control device. If, for example, the inspiratory valve is slow, the flow valve could be used for obtaining the most exact gas flow possible.

In a refinement of both embodiments the ventilator system in accordance with the invention, an additional detector can be installed in the patient tube between the breathing bag and the patient in order to measure one of the parameters of gas flow, temperature, relative gas humidity or concentration of a specific gas, the additional detector being connected to the control device for transmitting the measurement signal thereto. The control device ascertains whether the measurement signal meets at least a first defined condition, and the control device starts control of the flow of fresh gas in the patient tube when the measurement signal meets the first defined condition. Additionally or alternatively the control device can ascertain whether the measurement signal meets at least a second defined condition, whereby the control device sets the ventilator system in a safe state if the measurement signal meets the second defined condition.

In this way, a parameter other than the one controlling the flow of fresh gas can be used. For example, the detector can measure the $CO_2$ concentration in the gas in the patient tube. When it senses a concentration exceeding a defined first value, this indicates that the patient has begun expiration. A flow of gas could then be introduced to keep the patient from re-breathing any of her/his expired gas. Moreover, this would result in a monitoring of the ventilator system's function. If the new parameter's measurement signal meets certain conditions, e.g. that the $CO_2$ concentration does not exceed a defined second value for a specific period of time, the control device sets the ventilator system in a safe state. "Safe state" means that the device is transferred to a state in which it cannot harm the patient. This could mean, e.g. that an alarm is activated to attract the staff's attention so they can remedy some fault or replace the device. The device could even automatically perform some safety measure, such as opening a valve, changing the control parameter or changing the ventilation mode. Even when it performs an automatic safety measure, the device should appropriately emit an alarm. If a fault develops, such as a malfunction of a detector measuring the control parameter, another detector could be enabled for measuring the control parameter, or a signal from a detector measuring another parameter could be used instead as a control parameter, or the system could be switched to another ventilation mode, e.g. from manual to mechanical ventilation. In all instances, an alarm could be activated to call the staff's attention to the fault.

Preferably the control device includes a first comparator using the measurement signal and the first defined condition as input signals, the first comparator then generating an output signal when the measurement signal meets the first defined condition. The output signal activates the control device's regulation of the flow of fresh gas in the patient tube. The control device also then preferably includes a second comparator, which uses the measurement signal and the second defined condition as input signals, the second comparator generating an output signal if the measurement signal meets the second defined condition. This output signal is sent to an alarm generator to activate an alarm and/or a switch to switch control of the ventilator system to mechanical ventilation or to switch to the use of some other parameter.

DESCRIPTION OF THE DRAWINGS

FIG. 1 schematically shows a first embodiment of the ventilator system according to the invention.

FIG. 2 is a block diagram of a control device in the ventilator system.

FIG. 3 illustrates a first type of regulation the ventilator system is capable of performing.

FIG. 4 illustrates a second type of regulation the ventilator system is capable of performing.

FIG. 5 schematically shows a second embodiment of the ventilator system according to the invention.

DESCRIPTION OF THE PREFERRED EMBODIMENTS

The ventilator system 2 shown in FIG. 1 includes a ventilator unit 4, a patient tube and a breathing bag 8 (manual bag). Air can be supplied to a patient connected to the patient tube 6 in three ways: by spontaneous breathing, by mechanical ventilation via the ventilator unit 4 or by manual ventilation with the breathing bag 8. The ventilator unit 4 has a control panel 10 from which a plurality of parameters, gas mixtures and operating modes can be set with one or more of the knobs 12. For example, a resistance pressure (i.e. Positive End Expiratory Pressure—PEEP), the maximum permissible excess pressure in the patient tube 6, a pop-off pressure or a minimum permissible pressure in the breathing bag 8, i.e. filling pressure, can be set.

When the manual ventilation mode is set on the control panel 10, a breathing bag valve 14, which can be a manually adjustable valve, opens. A physician can compress the breathing bag 8 by squeezing it, thereby increasing pressure in the patient tube 6 so gas is forced into the patient's lungs. When the physician relaxes pressure on the breathing bag 8, gas can flow back, and the patient exhales. With this ventilation mode, the physician is continuously able to feel the action of the lungs and exercise complete control over the patient's respiration.

To keep the patient from re-breathing expired gas, the ventilator system 2 is controlled during spontaneous breathing and manual ventilation of the ventilator unit 4 in a special way. A pressure gradient detector 16 is installed between the breathing bag 8 and the patient tube 6, which measures the pressure difference at one measurement point, this pressure difference caused by the flow of gas to/from the breathing bag 8. The measurement signal from the pressure gradient detector 16 is sent to the ventilator unit 4 in which it is conditioned in a control device 18 shown in greater detail in FIG. 2.

The ventilator unit 4 also contains an inspiratory valve 26 and an expiratory valve 30, both controlled by the control device 18, and a first flow meter 32, a first pressure detector 33, a second flow meter 36 and a second pressure detector 40 whose respective measurement signals are sent to the control device 18.

The measurement signal from the pressure gradient detector 16, as shown in FIG. 2, first arrives at a first signal shaper 20 in which the signal is filtered, amplified and digitized before being sent to a microprocessor 22. The parameters set on the control panel 10 are also sent to the microprocessor 22.

When the microprocessor 22, according to the signal from the pressure gradient detector 16, determines that the patient has started expiration, i.e. a flow is detected into the breathing bag 8, it emits a first control signal which is sent to the inspiratory valve 26 via a first D/A converter 24, and a second control signal which is sent to the expiratory valve 30 via a second D/A converter 28. The valves 26 and 30 are opened to permit the passage of a flow of gas according to the control signals.

The flow of gas through the inspiratory valve 26 is measured in the first flow meter 32, whose measurement signal is sent to the microprocessor 22 via a second signal former 34. Here, inspiratory flow is regulated so it has the same magnitude as the expiratory flow from the patient. This is accomplished by registering influx into the breathing bag 8 at the onset of expiration, as described above. The control device 18 then opens the inspiratory valve 26 and the expiratory valve 30, regulating the respective flows in those valves so they are as close as possible to the expired flow. As a result, the flow of gas through the inspiratory valve 26 keeps the flow of expired gas from filling the breathing bag 8 and fills the breathing bag 8 with fresh gas. Expired gas is thereby forced out of the system through the expiratory valve. Changes in expiratory flow from the patient are immediately recorded by the pressure gradient detector 16, enabling the control unit 18 to correct control of the valves 26 and 30. The breathing bag 8 is thereby filled with fresh gas in a way which simulates the patient's expiration almost exactly, and it feels to the physician as if the patient were breathing directly into the breathing bag 8.

In order to control the expiratory valve 30 as accurately as possible, the flow of gas at the expiratory valve is measured in the second flow meter 36, and the measurement signal is sent to the microprocessor 22 via a third signal former 38.

To ensure that the breathing bag 8 fills with enough fresh gas, the microprocessor 22 can integrate the flows measured at the inspiration valve 26, the expiration valve 30 and the breathing bag 8. The integrals designate the volume of gas passed, and the control unit 18 can regulate the valves 26 and 30 so the volumes are of equal magnitude.

The pressure gradient detector 16 is in this embodiment zeroed continuously to increase the system's ability to measure small flows. This can be compared to an AC coupling with a long time constant, lasting up to several minutes. Here, volume can be integrated by digital sampling of the changes registered. The pressure gradient detector 16 is zeroed before the breathing bag valve 14 opens in order to supply an reference output for flow at the breathing bag 8. Moreover, pressure is measured in the patient tube 6 at the inspiratory valve 26 in the first pressure detector 33, whose measurement signal is fed to the microprocessor 22 via a fourth signal former 35. Pressure inside the breathing bag 8 can be determined when pressure in the patient tube 6 and the drop in pressure across the pressure gradient detector 16 are known. If pressure in the breathing bag 8 drops too much, additional fresh gas is supplied via the inspiratory valve 26.

The second pressure detector 40 is located by the expiratory valve 30 in the patient tube 6 and senses pressure at the expiratory valve 30. The measurement signal is sent to the microprocessor 22 via a fifth signal former 42. If pressure at the expiratory valve 30 exceeds a defined maximum pressure, i.e. the pop-off pressure, the expiratory valve 30 opens further in order to reduce excess pressure in the patient tube 6. The aim is to limit the build-up of pressure in the patient's lungs.

The microprocessor 22 can also control the breathing bag valve 14 via a third D/A converter 44. Use of this valve may be appropriate if the inspiratory valve 26 is not fast enough.

FIGS. 3 and 4 respectively schematically illustrate two ways in which the microprocessor 22 can control the valves 26 and 30. The signals are designated as follows: $P_{popoff}$ is the pop-off pressure, which is set on the control panel 10, $P_E$ is the pressure measured by the second pressure detector 40, $\Phi_E$ is the flow at the expiratory valve 30, $\Phi_H$ is the breathing bag flow 8, $\Delta P_H$ is drop in the pressure across the pressure gradient detector 16 in the breathing bag 8, $P_f$ is the filling pressure, which is set on the control panel 10, $P_{PEEP}$ is the end expiratory pressure, which is set on the control panel 10, $P_I$ is the pressure measured by the first pressure detector 33, $P_S$ is a defined minimum pressure during spontaneous breathing and $\Phi_{Iset}$ is the reference value for flow at the inspiratory valve 26.

A regulation sufficient for controlling the supply of fresh gas to the breathing valve 8 during the expiratory phase is illustrated in FIG. 3. The value for expiratory flow $\Phi_E$ and the value for breathing bag flow $\Phi_H$ are sent to a first adder 46. Outflow from the breathing bag 8 is defined as positive, and influx into the breathing bag 8 is defined as negative. The first adder 46 therefore forms the difference between the absolute values for the flows $\Phi_E$ and $\Phi_H$. This difference, which constitutes a fault signal, is sent to a first regulator 48 which sends a control signal to the expiratory valve 30 via the second D/A converter 28 in an effort to achieve an expiratory flow generating a fault signal having a value of zero, i.e. the flows $\Phi_E$ and $\Phi_H$ are to have the same absolute value. The value for the breathing bag flow $\Phi_H$ is inverted in an inverter 49, thereby constituting a reference value $\Phi_{Iset}$ for inspiratory flow. Inversion is performed because of the above definition for flow directions.

In FIG. 4, regulation according to FIG. 3 has been augmented with a plurality of monitoring functions and additional control refinements. Thus, in the same way as in FIG. 3, the $\Phi_H-\Phi_E$ difference is determined in the first adder 46 to form a fault signal used by the a 48 to control the expiratory valve 30. Pressure $P_E$ in the patient tube 6 at the expiratory value 30 is monitored at the same time. In a second adder 50, the pressure $P_E$ is subtracted from the pop-off pressure $P_{popoff}$. If the measured pressure $P_E$ exceeds the pop-off pressure $P_{popoff}$, i.e. a negative fault signal, a first regulator/logic unit 52 first switches a first switch 54, and then assumes control of the expiratory valve 30.

Another monitoring which is performed concerns pressure in the breathing bag 8. As previously noted, the filling pressure $P_f$ can be set on the control panel 10. This corresponds to the lowest permissible pressure in the breathing bag 8. If pressure in the breathing bag drops below the filling pressure $P_f$, the inspiratory valve 26 will admit an additional influx of fresh gas to fill the breathing bag B. A separate pressure detector can be installed in the breathing bag 8 in order to determine the pressure $P_H$ therein, but the present embodiment utilizes the relationship between pressure in the inspiratory line $P_I$, the drop in pressure $\Delta P_H$ across the pressure gradient detector 16 and pressure $P_H$ in the breathing bag 8, i.e. $P_I = P_H - \Delta P_H$. The pressure gradient $\Delta P_H$ is defined as positive when $\Phi_H$ is positive, i.e. when gas flows out of the breathing bag 8. This means that $P_H = P_I + \Delta P_H$. For the breathing bag 8 to fill at the right pressure when an end expiratory pressure $P_{PEEP}$ is present, the value for the filling pressure $P_f$ is incremented by the value for the end expiratory pressure $P_{PEEP}$. Thus, the pressure $P_f+P_{PEEP}-\Delta P_H$ is compared in a third adder 56 to the pressure $P_I$ measured in the patient tube 6 at the inspiratory valve 26. The fault signal thus obtained is sent to a second regulator/logic unit 58 capable of changing the reference value $\Phi_{Iset}$ for the inspiratory flow. Therefore the flow value $\Phi_H$ is also supplied to the second regulator/logic unit 58. Pressure $P_H$ in the breathing bag 8 is normally sufficient, and the value for $\Phi_{Iset}$ is equal to the value for $\Phi_H$, but if the pressure $P_I$ drops below the pressure $P_f+P_{PEEP}-\Delta P_H$, which, as noted above, means that pressure $P_H$ in the breathing bag 8 has dropped too much, the reference value $\Phi_{Iset}$ is changed so more fresh gas is fed into the breathing bag 8.

In the event that the patient begins breathing spontaneously, a second switch 60 is automatically switched, via the second regulator/logic unit 58, to a defined regulatory pressure $P_S$ for the supplementary supply of fresh gas. In principle, this means only that a supplementary supply of fresh gas is avoided during the inspiratory phase when pressure in the breathing bag 8 drops because the patient takes a breath. $P_S$ is typically 5 cm $H_2O$ below atmospheric pressure. During the expiratory phase, the system again automatically switches to nominal pressure regulation. This takes place when the second regulator/logic unit 58 registers a change in the direction of the breathing bag flow $\Phi_H$.

Control of the second switch 60 can be accomplished by the second regulator/logic unit 58, which has $\Phi_H$ and the pressure gradient $P_{PEEP}+P_f-\Delta P_H-P_I$ as input signals, sends a signal to switch the second switch 60 when $\Phi_H > 3$ l/min (a positive $\Phi_H$ represents an outflow according the definition above) and $P_I<(P_f+P_{PEEP}-\Delta P_H)$, i.e. when spontaneous breathing is deemed to be present.

The ventilator system 2 can also be controlled so it supplies a flow of gas passing through the patient tube 6 during expiration, during inspiration or during both expiration and inspiration. This flow of gas flushes expired gas out of the system, thereby reducing the system's dead space. To facilitate control of this flow of gas when the breathing bag 8 is filled, pressure in the system can either be regulated against the filling pressure $P_f$ for the breathing bag or against the system's maximum pressure $P_{popoff}$.

In the first instance, inspiratory flow is regulated so it is less than expiratory flow. For example, the flushing flow at the inspiratory valve could be reduced to 2 liters/minute when the total flushing flow is 3 liters/minute, and the imposed, controlled flow to fill the breathing bag 8 is reduced by 4% of the amplitude value for flow to the breathing bag 8. The expiratory flow ($\Phi_E$) can simultaneously be increased by 5% of the flow to the breathing bag 8. When pressure in the breathing bag 8, corresponding to $P_f+\Delta P_H$, drops below the filling pressure $P_f$ plus the end expiratory 5 pressure $P_{PEEP}$, the inspiratory valve 26 opens to fill the breathing bag 8.

In the second instance, when the system is regulated against exceeding the popoff pressure $P_{popoff}$, inspiratory flow is instead increased so it is greater than expiratory flow. When pressure in the patient tube $P_E$ exceeds pop-off pressure $P_{popoff}$, the expiratory valve 30 opens to bleed off surplus gas.

Since all flows are measured or calculated in the ventilator system 2, the microprocessor 22 can quickly determine whether the patient should be disconnected from the system, then stopping all gas flows. This is particularly important in conjunction with the administration of a gaseous anesthetic to a patient, since it would prevent the release of anesthetic into the operating theater.

In the corresponding manner, leakage from different parts of the system can be easily detected. Regulation of the entire system can even be managed according to readings from pressure sensors, since pressure and flow in the system are directly interrelated, and the value of one can be established from the value for the other.

A digitally controlled system has been described in the embodiment, but the system can also be devised as an analog circuit.

A second embodiment of the ventilator system is shown in FIG. 5. The ventilator system 64 in FIG. 5 includes a ventilator unit 66, which could be, e.g., a Servo Ventilator 300 manufactured by Siemens-Elema AB, a patient tube 68 connected to the ventilator unit 66 and a patient and a breathing bag 70. A control device 72 is connected to the ventilator unit 66 and breathing bag 70, to control the filling of the breathing bag 70 with fresh gas during manual ventilation of the patient.

From the ventilator unit 66, a plurality of measured parameters is sent to the control device 72. Expiratory flow $\Phi_E$ is transmitted via a first signal line 74, expiratory pressure $P_E$ is transmitted via a second signal line 76, inspiratory flow $\Phi_I$ is transmitted via a third signal line 78 and inspiratory pressure $P_I$ is transmitted via a fourth signal line 80. A pressure gradient detector 82 is located in the breathing bag 70. The measurement signal from the detector 82 is sent to the control device 72 via a fifth signal line 84.

In principle, the ventilator unit 66 is divided into two sections, an inspiratory section 66A and an expiratory section 66B. In the inspiratory section 66A there is an inspiration valve 86 which regulates the flow of gas into the patient tube 68, and in the expiratory section 66B there is an expiratory valve 88 which regulates the flow of gas out of the patient tube 68. A number of control lines are installed between the control device 72 and the ventilator unit 66 for controlling the valves 86 and 88. Control signals for the ventilation phases, i.e. whether the valves 86 and 88 are to be open or closed and whether the valves 86 and 88 are to be controlled according to pressure or flow, are sent to the ventilator unit 66 via first control line 90. When the valves 86 and 88 are to be controlled according to flow, a first flow control signal is sent to the inspiratory section 66A via a second control line 92, and a second flow control signal is sent to the expiratory section 66B via a third control line 94. When the valves 86 and 88 are to be controlled according to pressure, a first pressure control signal is sent to the inspiratory section 66A via a fourth control line 96, and a second pressure control signal is sent to the expiratory section 66B via a fifth control line 98.

The control device 72 can perform the regulation and control described in conjunction with FIGS. 1–4.

The ventilator system 64 functions as follows: In normal ventilation, a breathing bag valve 108 is closed, and the system operates like a conventional ventilator. The breathing bag valve 108 is open in manual ventilation of the patient. During the inspiratory phase, the control device 72 controls the ventilator unit 66 so the inspiratory valve 86 and the expiratory valve 88 are closed. The patient's inspiration is monitored by the physician who squeezes the breathing bag 70 which, since the valves 86 and 88 are closed, is in direct contact, like a communicating vessel, with the patient's lungs. During inspiration, the physician can therefore feel the pressure in the patient's lungs in the breathing bag 70.

During expiration, the physician relaxes pressure on the breathing bag 70. As a result, pressure in the breathing bag 70 drops, and gas begins to flow into the bag. As noted above, this flow is measured by the pressure gradient detector 82, and the measurement signal is sent to the control device 72 which now controls the ventilator unit 66 so the inspiratory valve 86 and the expiratory valve 88 admit an inspiratory flow and an expiratory flow of the same magnitude as the flow measured by the gradient pressure detector 82. The breathing bag 70 then fills with fresh gas from the inspiratory valve 86. The patient's expired gas is thereby unable to flow into the breathing bag 70 and is conducted away through the expiratory valve 88. Gas outflow through the expiratory valve 88 has the same flow profile as when the patient's lungs are emptied of gas. Thus, the patient's lungs, even during expiration, will also feel to the physician as though they were communicating directly with the breathing valve 70, even though the expired volume is controlled via the expiratory valve 88. In other words, the physician controls the patient's respiration during both inspiration and expiration with the aid of the breathing bag 70.

If the inspiratory flow momentarily drops below the flow at the gradient pressure detector 82, the control device 72 controls the ventilator unit 66 such that the volume of inspiratory flow during the expiratory phase is caused to correspond to at least the volume of flow into the breathing bag 70 during the same expiratory phase. This regulatory method effectively prevents the patient's expired gas from reaching the breathing bag 70. The inspiratory flow can even be allowed to remain constant, provided its magnitude is always greater than the magnitude of flow into the breathing bag 70 when the breathing bag 70 is released by the physician. According to the above-described principle, constant flows of gas from an external source of gas can be connected to the system.

In order to enhance patient safety, the ventilator system 64 contains a $CO_2$ detector 100 placed in the patient tube 68 near the patient. The measurement signal is sent to the control device 72 via a sixth control line 102. During expiration, the $CO_2$ detector 100 registers the $CO_2$ content of the patient's expired air and can then monitor the content, activating an alarm when the value deviates from normal levels. The $CO_2$ content should drop to zero, or close to zero, during inspiration, since expired gas is replaced with fresh gas. If this is not the case, there is some fault in the system, and the alarm is activated. To ensure that the alarm is triggered, even if the gradient pressure detector 82 ceases to operate and fails to register any flow, time conditions can be set for the duration of expiration, i.e. something is wrong if a defined $CO_2$ concentration is measured over a defined period of time, thereby activating the alarm.

Since $CO_2$ content rises very steeply when the patient begins exhaling, this circumstance can be used to trigger the system to start refilling the breathing bag 70 with fresh gas. The filling procedure can be controlled in the way described above.

A direction-dependent flow meter 104 placed in the patient tube 68 between the breathing bag 70 and the patient is an alternative, or a complement, to the $CO_2$ detector 100. The measurement signal is sent to the control device 72 via a seventh signal line 106. The direction-dependent flow meter 104 senses gas flows toward the breathing valve 70. The direction-dependent flow meter 104 should only intermittently detect flow during the expiratory phase when regulation of fresh gas replenishment is working properly. The counterflow of fresh gas from the inspiratory section 66A should then impede expiratory flow towards the breathing bag 70, forcing evacuation of expired gas via the expiratory section 66B. The direction-dependent flow meter 104 will not detect any flow until the patient begins exhaling and when there is an increase in expiratory flow from the patient. Detection by the direction-dependent flow meter 104 of a given flow, or a detection lasting a given period of time, e.g. a few seconds, indicates that the system is not working properly, and an alarm is activated.

The measurement signal from the direction-dependent flow meter 104 can also be used to start control of fresh gas replenishment.

In addition to issuing an alarm, the control device 72 can switch the operating mode of the ventilator unit 66 from manual ventilation to mechanical ventilation when a fault occurs so the patient's respiration can still be sustained.

Alternately, the control device 72 can shift to controlling the ventilator system 64 according to some other control parameter, such as the measurement signal from the direction-dependent flow meter 104. This control redundancy for the control device 72 optimizes the functioning and patient safety of the ventilator system 64.

The $CO_2$ detector 100 can be replaced, without any change in function, with some other gas meter, e.g. an $O_2$ detector or an anesthetic meter during anesthesia. Air expired by the patient would then contain lower concentrations of fresh gas, since the patient's body absorbs a certain amount of $O_2$ and anesthetic gas in each respiratory cycle. Other types of detectors which could replace the $CO_2$ detector are a thermometer, hygrometer and direction-dependent flow meter. The direction-dependent flow meter 104 can be replaced in the corresponding way, without any change in function, with a gas detector, thermometer or hygrometer.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for ventilating a patient comprising the steps of:

connecting an automatically operating ventilator end a manually operable breathing bag to airways of a patient;

manually squeezing said breathing bag in an inspiration phase to impose an inspiration on the patient and subsequently manually relaxing squeezing of said breathing bag to permit exhalation by, the patient of a flow of expired gas during an expiration phase;

non-manually feeding fresh gas from said ventilator into said breathing bag during said expiration phase with a flow corresponding to said flow of expired gas; and conducting said flow of expired gas out of said ventilator system.

2. A method as claimed in claim 1 comprising the additional steps of:

measuring a parameter related to the expiration of the patient at a location between the patient and said breathing bag; and controlling said flow of fresh gas dependent on said parameter.

3. A method as claimed in claim 2 wherein the step of measuring a parameter related to the expiration of the patient is further defined by measuring one of the parameters of said flow of expired gas, the temperature of said expired gas, the relative humidity of said expired gas or the concentration of a selected gas in said expired gas.

4. A method as claimed in claim 2 comprising the additional steps of:

measuring an additional, separate parameter related to the expiration of said patient for starting the controlling of said flow of fresh gas; and taking a remedial step if said additional, separate parameter meets at least one defined condition.

5. A method as claimed in claim 4 wherein the step of taking a remedial step is further defined by generating an alarm.

6. A method as claimed in claim 4 wherein the step of taking a remedial step is further defined by switching to an alternative ventilation mode.

7. A method as claimed in claim 2 comprising the additional steps of:

measuring an additional, separate parameter for starting a functional check on the ventilation of said patient; and taking a remedial step if said functional check meets at least one defined condition.

8. A method as claimed in claim 7 wherein the step of taking a remedial step is further defined by generating an alarm.

9. A method as claimed in claim 7 wherein the step of taking a remedial step is further defined by switching to an alternative ventilation mode.

10. A ventilator system comprising:

a patient tube connectable to a patient;

ventilator means, connected to said patient tube, for non-manually controlling a flow of gas in the patient tube to ventilate a patient;

a breathing bag connected to said patient tube for manually controlling a flow of gas in the patient tube for ventilating a patient;

parameter detector means for sensing a parameter related to respiration of a patient;

control means in said ventilator means for controlling said flow of gas in said patient tube dependent on the parameter sensed by said parameter detector means for feeding a flow of fresh gas, during expiration by a patient, into said breathing bag corresponding to a flow of gas expired by a patient; and means for conducting said gas expired by a patient out of said ventilator system.

11. A ventilator system as claimed in claim 10 wherein said parameter detector means comprises means for sensing gas flow into said breathing bag.

12. A ventilator system as claimed in claim 10 wherein said parameter detector means comprises means for sensing gas flow from said breathing bag.

13. A ventilator system as claimed in claim 10 wherein said parameter detector means comprises means for sensing gas pressure in said breathing bag.

14. A ventilator system as claimed in claim 10 wherein said parameter detector means is disposed between a patient and said breathing bag, and wherein said parameter detector means comprises means for sensing a parameter related to expiration by a patient.

15. A ventilator system as claimed in claim 14 wherein said parameter detector means comprises means for sensing one of the parameters of the flow of said gas expired by a patient, the temperature of said gas expired by said patient, the relative humidity of said gas expired by a patient or the concentration of a selected gas in said gas expired by a patient.

16. A ventilator system as claimed in claim 10 further comprising:

a controllable inspiratory valve disposed at a first end of said patient tube;

a controllable expiratory valve disposed at a second, opposite end of said patient tube; and wherein said control means comprises means for controlling said controllable inspiratory valve and said controllable expiratory valve dependent on said parameter.

17. A ventilator system as claimed in claim 16 wherein said parameter detector means comprises a first detector means, and said ventilator system further comprising:

second detector means for sensing gas flow at said inspiratory valve;

third detector means for sensing gas flow at said expiratory valve, each of said first, second and third detector means generating an output signal; and said control means including means for combining said output signals of said first, second and third detector means to obtain a combined signal, and for controlling said flow of gas in said patient tube dependent on said combined signal.

18. A ventilator system as claimed in claim 17 further comprising integrator means for integrating each of said output signals of said first, second and third detector means to determine the respective volumes of gas passing each of said first, second and third detector means, and wherein said means for combining comprises means for comparing said gas volumes and wherein said control means includes means for controlling said flow of gas in said patient tube so as to maintain each of said gas volumes substantially equal.

19. A ventilator system as claimed in claim 18 wherein said control means includes means for continuously zeroing said first detector means.

20. A ventilator system as claimed in claim 16 wherein said parameter detector means comprises a first detector means, and said ventilator system further comprising:

second detector means for sensing gas pressure at said inspiratory valve;

third detector means for sensing gas pressure at said expiratory valve, each of said first, second and third detector means generating an output signal; and said control means including means for combining said output signals of said first, second and third detector means to obtain a combined signal, and for controlling said flow of gas in said patient tube dependent on said combined signal.

21. A ventilator system as claimed in claim 20 wherein said control means includes means for continuously zeroing said first detector means.

22. A ventilator system as claimed in claim 16 wherein said control means comprises means for controlling said controllable inspiratory valve and said controllable expiratory valve for passing a flow of fresh gas through said patient tube during expiration by a patient.

23. A ventilator system as claimed in claim 22 wherein said control means comprises means for controlling said controllable inspiratory valve and said controllable expiratory valve for maintaining a flow of gas at said inspiratory valve less than a flow of gas at said expiratory valve, wherein said parameter detector means comprises means for measuring pressure in said breathing bag, and wherein said control means includes means for controlling said inspiratory valve, when pressure in said breathing bag falls below a defined pressure, to feed a flow of gas into said patient tube for filling said breathing bag.

24. A ventilator system as claimed in claim 22 wherein said control means comprises means for controlling said controllable inspiratory valve and said controllable expiratory valve for maintaining a flow of gas at said inspiratory valve greater than a flow of gas at said expiratory valve, and further comprising further parameter detector means for measuring pressure in said patient tube, and said control means including means for controlling said expiratory valve, when pressure in said patient tube exceeds a predetermined pressure, for causing said pressure in said patient tube to drop.

25. A ventilator system as claimed in claim 16 wherein said control means comprises means for controlling said controllable inspiratory valve and said controllable expiratory valve for passing a flow of fresh gas through said patient tube during inspiration by a patient.

26. A ventilator system as claimed in claim 25 wherein said control means comprises means for controlling said controllable inspiratory valve and said controllable expiratory valve for maintaining a flow of gas at said inspiratory valve less than a flow of gas at said expiratory valve, wherein said parameter detector means comprises means for measuring pressure in said breathing bag, and wherein said control means includes means for controlling said inspiratory valve, when pressure in said breathing bag falls below a defined pressure, to feed a flow of gas into said patient tube for filling said breathing bag.

27. A ventilator system as claimed in claim 25 wherein said control means comprises means for controlling said controllable inspiratory valve and said controllable expiratory valve for maintaining a flow of gas at said inspiratory valve greater than a flow of gas at said expiratory valve, and further comprising further parameter detector means for measuring pressure in said patient tube, and said control means including means for controlling said expiratory valve, when pressure in said patient tube exceeds a predetermined pressure, for causing said pressure in said patient tube to drop.

28. A ventilator system as claimed in claim 10 further comprising:

further parameter detector means for generating a measurement signal corresponding to a measurement of one of the parameters of gas flow of gas expired by a patient, temperature of gas expired by said patient, relative humidity of gas expired by a patient, or the concentration of a selected gas in gas expired by a patient, said measurement signal being supplied to said control means; and said control means comprising means for determining whether said signal meets a defined condition and for starting control of said gas flow in said patient tube when said measurement signal meets said defined condition.

29. A ventilator system as claimed in claim 28 wherein said control means includes comparator means having said measurement signal and a signal corresponding to said defined condition as input signals for comparing said measurement signal to said signal corresponding to said defined condition, and for generating an output signal enabling controlling of said flow of gas by said control means in said patient tube.

30. A ventilator system as claimed in claim 10 further comprising:

further parameter detector means for generating a measurement signal corresponding to a measurement of one of the parameters of gas flow of gas expired by a patient, temperature of gas expired by said patient, relative humidity of gas expired by a patient, or the concentration of a selected gas in gas expired by a patient, said measurement signal being supplied to said control means; and said control means including means for determining when said measurement signal meets a defined condition and for setting said ventilatory system in a safe state if said measurement signal meets said defined condition.

31. A ventilator system as claimed in claim 30 wherein said control means includes comparator means supplied with said measurement signal and a signal corresponding to said defined condition as input signals for comparing said measurement signal with said signal corresponding to said defined condition, and for generating an output signal causing said ventilator system to be placed in said safe state dependent on the comparison.

32. A ventilator system as claimed in claim 31 wherein said means for setting said ventilator system in a safe state comprises means for generating an alarm signal.

33. A ventilator system as claimed in claim 31 wherein said means for setting said ventilator system in a safe state comprises means for switching said ventilator system to an alternative ventilation mode.

34. A ventilator system as claimed in claim 10 further comprising:

further parameter detector means for generating a measurement signal corresponding to a measurement of one of the parameters of gas flow of gas expired by a patient, temperature of gas expired by said patient, relative humidity of gas expired by a patient, or the concentration of a selected gas in gas expired by a patient, said measurement signal being supplied to said control means;

said control means comprising means for determining whether said signal meets a first defined condition and for starting control of said gas flow in said patient tube when said measurement signal meets said first defined condition, and said control means further including means for determining whether said measurement signal meets a second defined condition and for setting said ventilator system in a safe state if said measurement signal meets said second defined condition.

35. A ventilator system as claimed in claim 34 wherein said control means includes:

first comparator means supplied with said measurement signal and a signal corresponding to said first defined condition as input signals for comparing said measurement signal with said signal corresponding to said first defined condition, and for generating an output signal enabling controlling of said flow of gas by said control means in the patient tube when said measurement signal equals said signal corresponding to said first defined condition, and second comparator means supplied with said measurement signal and a signal corresponding to said second defined condition as input signals for comparing said measurement signal with said signal corresponding to said second defined condition, for generating a further output signal causing said control means to set said ventilator system in said safe state if said measurement signal equals said signal corresponding to said second defined condition.

36. A ventilator system as claimed in claim 34 wherein said means for setting said ventilator system in a safe state comprises means for generating an alarm signal.

37. A ventilator system as claimed in claim 34 wherein said means for setting said ventilator system in a safe state comprises means for switching said ventilator system to an alternative ventilation mode.

* * * * *